June 9, 1942. E. H. SCHULTZ Plant Pat. 527
PHLOX
Filed Oct. 31, 1941
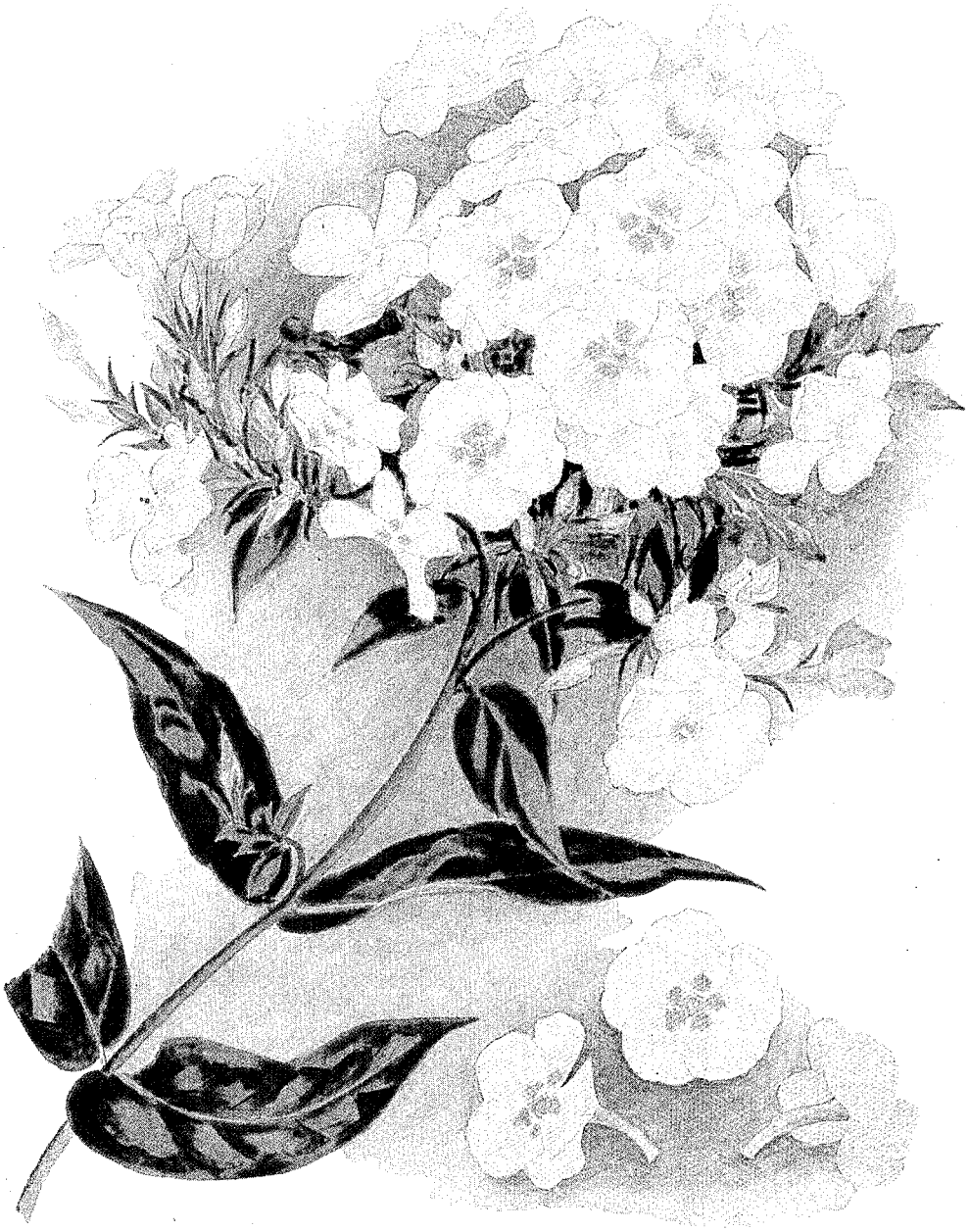
WITNESS
Addison E. Avery
INVENTOR
ELMER H. SCHULTZ
BY John H. Brennan,
his ATTORNEY Patented June 9, 1942

Plant Pat. 527

UNITED STATES PATENT OFFICE

527

PHLOX

Elmer H. Schultz, Mentor, Ohio, assignor to The Wayside Gardens Company, Mentor, Ohio, a corporation of Ohio Application October 31, 1941, Serial No. 417,320

1 Claim. (Cl. 47—60)

This invention relates to a new and distinct variety of *phlox decussata*.

The new variety was produced by me by crossing the *phlox decussata* known as Leo Schlageter, as the seed parent, with the *phlox decussata* known as Europa, as the pollen parent.

The new variety was first produced by me in 1938 at The Wayside Gardens nursery in Mentor, Ohio. It was subsequently asexually reproduced by me first in 1939 at which time about one hundred plants were asexually reproduced from root cuttings of the original. In 1940 and since about eleven hundred plants were asexually reproduced from root cuttings of the original plant and of the first reproductions. All of the asexual reproductions were true to the original.

The plant has a fibrous mass of roots which are very strong and in the form of a heavy clump, they are relatively large for this type of plant and are very vigorous in lateral growth. The resistance of the roots and the plant generally to diseases, wetness and drouth is excellent, as also is the winter resistance. The plant thrives in any good garden soil.

The exposed plant is herbaceous, generally upright, dense and compact. The plant grows to an unusual height of from four to six feet and, except for the size, is of the usual shape of a *phlox decussata*. The growth is extremely vigorous and the exposed plant structure is exceedingly resistant to disease, drouth, wetness, and mildew. The plant prefers moderate sun, or partial shade, with normal drainage.

The plant consists essentially of stiff, upright herbaceous stalks, each of which grows singly from the root clump with substantially no branches. The stalks are adequate to support the bloom well and are exceedingly tough, but not brittle. They withstand extremely high winds without breaking or damage. Generally, they are a reddish green, comparable to Maerz and Paul Plate No. 6–J–1 on the upper side and light green, comparable to Maerz and Paul Plate No. 19–J–5, on the under side. The color is generally uniform. The stalks measure from four to six feet high on the average and are smooth in texture.

The foliage is relatively dense, the leaves generally being arranged oppositely, the pair often being spiralled about the stalk with respect to each other. They are abundant in quantity. The older leaves are close to Brunswick and Civette green on the upper surface, comparable to Maerz and Paul Plate No. 22–L–9. On the under surface they are a lighter green. The newer leaves are green, tipped with a color comparable to Maerz and Paul Plate No. 6–J–1. The leaves are large for this type of plant, being about twenty percent larger than the average. They are of the usual lanceolate shape with tapering bases, acute apices and entire margins. They are relatively heavy and thick and smooth on the upper and lower faces. Their persistence on the plant is excellent.

For both growth and flowering, the plants prefer moderate shade or partial sun but do well under the usual sun and shade conditions in which other varieties of phlox grow effectively.

The blooming period extends from the middle of July to the end of September, the plant blooming continuously during the period. The buds are of the usual type except they are relatively large. They are borne generally upright or leaning. When the sepals first divide the exposed portions of the petals are almost white but when the petals begin to unfurl the tips of the buds are approximately Cosmos or Persian Rose, comparable to Maerz and Paul Plate No. 50–C–7.

The peduncles vary in length with the age of the plant. The inflorescence is compound, being, in the young plant, roughly cylindrical and elongated but tapered to a point at the upper end. This shape varies, however, becoming somewhat globular as the plant increases in age and in a two or three year old plant the head is distinctly globular though somewhat elongated. The flower heads are very large, being almost twice the size of any other phlox and ranging from twelve to sixteen inches across.

The drawing shows a portion only of the inflorescence, due to the fact that it would be impossible to show the true size of the entire head in a patent drawing and a proportional reduction in size would necessitate a showing of the individual florets at such a scale that the details thereof would not be presented effectively.

The three individual florets shown in the lower right hand corner of the drawing, separate and apart from the plant, are of true average size and they are larger than those of other *phlox decussata*. Likewise, the number of florets in a head is almost double the number in a head of other *phlox decussata*. In addition there are a large number of buds as a result of which the blooming season is prolonged considerably beyond the average for *phlox decussata*.

The permanence of the florets on the plant is excellent and far above the average. The permanence of the florets as a cut flower far exceeds anything yet obtained in phlox. The florets do not burn in the sun and they are little affected by rain or high winds.

The petals on each floret range through a number of related colors or shades from their outer margins inwardly. The outer margins are a light pink, comparable to Maerz and Paul Plate No. 2–A–2, which blends into a purple rose, comparable to Maerz and Paul Plate 2–H–5, a short distance inwardly. The purple rose, in turn, blends into Gladiolus, comparable to Maerz and Paul Plate 2–K–5 about midway between the outer margins and the bend at the top of the throat of the floret. Between the red area and the throat of the floret is an eye of dark purple red, comparable to Maerz and Paul Plate 53–L–7, this eye extending inwardly to the bend where the petals begin to converge to form the throat of the floret. The interior of the top of the throat is a violet purple, comparable to Maerz and Paul Plate No. 50–C–7, this color being visible as a slight ring at the bend in the petal of a fully open floret.

The under sides of the petals are cameo pink, comparable to Maerz and Paul Plate No. 50–C–2, striped or mottled with a color comparable to Maerz and Paul Plate No. 51–H–4.

The tips of the large buds are a color comparable to Maerz and Paul Plate No. 50–C–7.

From the purple red eye, veins of the same color radiate faintly into the more outward portions of the petals. The color of the eye develops and intensifies from day to day throughout the blooming period.

The petals are of smooth texture, generally flat or very slightly curving. Each floret has the usual number and arrangement of petals, but the petals are of unusually large size.

The flowers have a strong fragrance of good quality which is very lasting both in the cut and uncut flowers. The unusual characteristics of the plant are its exceeding vigor, strength, and height; the resistance of the foliage to mildew and the general resistance of the plant to diseases; the compelling brilliant coloring of the flower heads and individual florets, the size of the heads and of the individual florets, the exceptionally long blooming period, and the excellent and almost unbelievable permanence of the flower both on the growing plant and as a cut flower.

Having now fully shown and described my new variety of rose and the mode of its production, what I claim and desire to secure by Letters Patent of the United States is:

The variety of *phlox decussata* herein shown and described characterized by the exceptionally large flower heads and individual florets, the brilliant color of the flower heads and individual florets, the exceptionally long blooming period, the excellent permanence of the flower both on the growing plant and as a cut flower, the resistance of the foliage to mildew and the general resistance of the plant to diseases, the exceeding vigor, strength and height of the plant.

ELMER H. SCHULTZ.